(12) United States Patent
Rezach

(10) Patent No.: US 12,114,899 B2
(45) Date of Patent: Oct. 15, 2024

(54) SPINAL IMPLANT AND METHOD

(71) Applicant: Warsaw Orthopedic, Inc., Warsaw, IN (US)

(72) Inventor: William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/847,613

(22) Filed: Jun. 23, 2022

(65) Prior Publication Data

US 2023/0414257 A1 Dec. 28, 2023

(51) Int. Cl.
*A61B 17/70* (2006.01)
*A61B 17/00* (2006.01)

(52) U.S. Cl.
CPC ............... *A61B 17/7052* (2013.01); *A61B 2017/00477* (2013.01)

(58) Field of Classification Search
CPC ............ A61B 17/7043; A61B 17/7041; A61B 17/7049; A61B 17/7052; A61B 17/7007; A61B 17/7008
See application file for complete search history.

(56) References Cited

U.S. PATENT DOCUMENTS

| | | | |
|---|---|---|---|
| 5,209,752 A | 5/1993 | Ashman et al. | |
| 5,499,983 A | 3/1996 | Hughes | |
| 6,001,098 A | 12/1999 | Metz-Stavenhagen et al. | |
| 6,231,575 B1 | 5/2001 | Krag | |
| 6,551,318 B1 | 4/2003 | Stahurski | |
| 7,585,312 B2 | 9/2009 | Rawlins et al. | |
| 7,753,940 B2 * | 7/2010 | Veldman | A61B 17/7041 606/278 |
| 7,922,746 B2 | 4/2011 | Miller | |
| 8,414,623 B2 | 4/2013 | Baker et al. | |
| 8,668,721 B2 * | 3/2014 | Miller | A61B 17/7055 606/264 |
| 8,715,323 B2 | 5/2014 | Ballard et al. | |
| 9,017,386 B2 | 4/2015 | Rezach | |
| 9,101,405 B2 | 8/2015 | Dickinson et al. | |
| 9,956,008 B2 * | 5/2018 | Agarwal | A61B 17/7035 |
| 10,321,939 B2 | 6/2019 | Lee et al. | |

(Continued)

FOREIGN PATENT DOCUMENTS

FR 2870713 A1 * 12/2005 ......... A61B 17/7035

OTHER PUBLICATIONS

International Search Report and Written Opinion of the International Searching Authority, PCT/IB2023/056094 European Patent Office, P.B. 5818 Patentlaan 2, NL 2280 HV Rijswijk, mailed Oct. 2, 2023.

*Primary Examiner* — Julianna N Harvey
(74) *Attorney, Agent, or Firm* — Sorell, Lenna & Schmidt, LLP

(57) ABSTRACT

A spinal implant includes a post with a receiver having a first mating surface and a stop. A connector defines an implant cavity. The connector includes a base having a second mating surface being positionable with the first mating surface to attach the connector with the receiver. The base defines a transverse passageway. A securing element is disposable in the passageway and engageable with the stop. In some embodiments, systems, surgical instruments, implants and methods are disclosed.

19 Claims, 15 Drawing Sheets

(56) References Cited

U.S. PATENT DOCUMENTS

| | | | |
|---|---|---|---|
| 2005/0113830 A1* | 5/2005 | Rezach | A61B 17/7037 606/60 |
| 2006/0079892 A1 | 4/2006 | Roychowdhury et al. | |
| 2006/0129150 A1 | 6/2006 | Suzuki et al. | |
| 2006/0247628 A1* | 11/2006 | Rawlins | A61B 17/7041 606/264 |
| 2007/0055239 A1* | 3/2007 | Sweeney | A61B 17/7037 606/86 A |
| 2007/0162008 A1* | 7/2007 | Cline | A61B 17/7041 606/60 |
| 2008/0021454 A1 | 1/2008 | Chao et al. | |
| 2008/0021455 A1 | 1/2008 | Chao et al. | |
| 2008/0021456 A1 | 1/2008 | Gupta et al. | |
| 2008/0195122 A1 | 8/2008 | Castellvi et al. | |
| 2010/0030275 A1 | 2/2010 | Winslow et al. | |
| 2010/0049253 A1 | 2/2010 | Miller | |
| 2011/0098748 A1 | 4/2011 | Jangra | |
| 2012/0029571 A1* | 2/2012 | Schwab | A61B 17/705 606/278 |
| 2012/0109210 A1* | 5/2012 | Baker | A61B 17/705 606/264 |
| 2012/0179205 A1* | 7/2012 | Miller | A61B 17/7041 606/279 |
| 2013/0150895 A1 | 6/2013 | McLean et al. | |
| 2013/0184760 A1* | 7/2013 | Ballard | A61B 17/7038 606/279 |
| 2013/0211456 A1* | 8/2013 | Dickinson | A61B 17/7038 606/279 |
| 2013/0245690 A1* | 9/2013 | Bridwell | A61B 17/7041 606/279 |
| 2018/0271563 A1* | 9/2018 | Protopsaltis | A61B 17/7041 |
| 2018/0360502 A1* | 12/2018 | Kim | A61B 17/7049 |
| 2019/0298422 A1* | 10/2019 | Rezach | A61B 17/7002 |
| 2021/0177468 A1 | 6/2021 | Murray | |

* cited by examiner

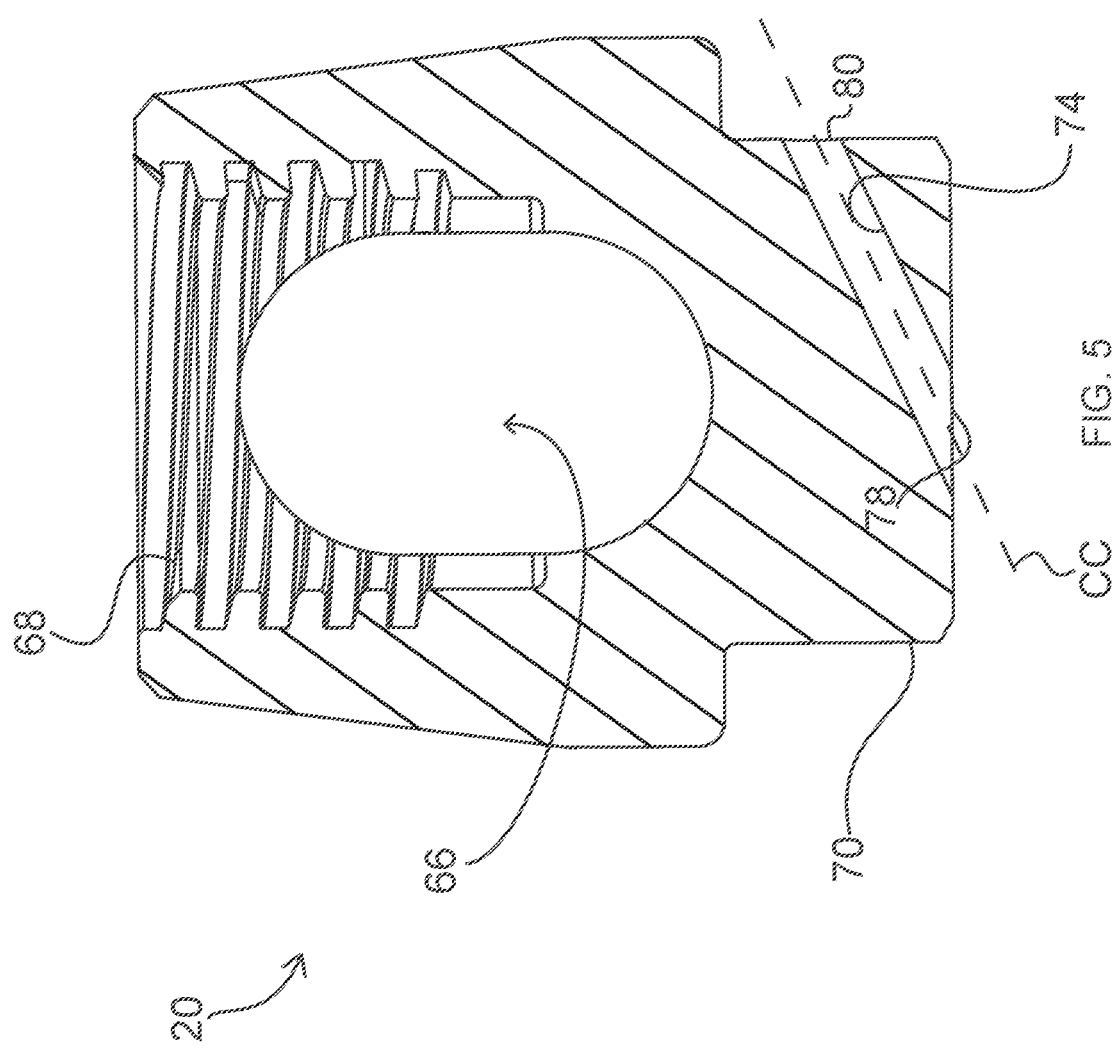

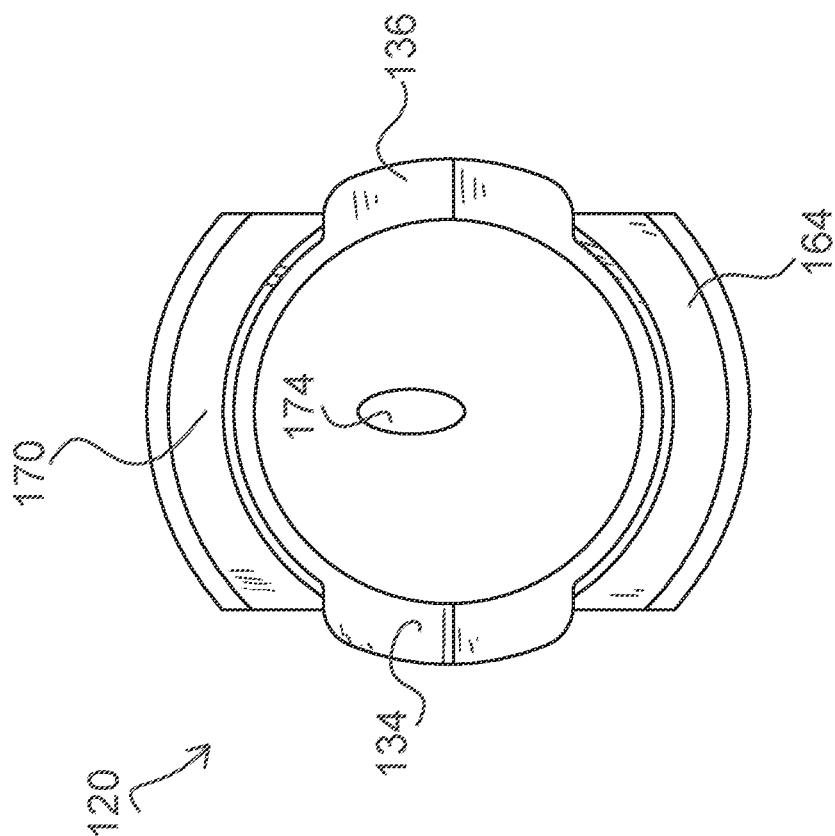
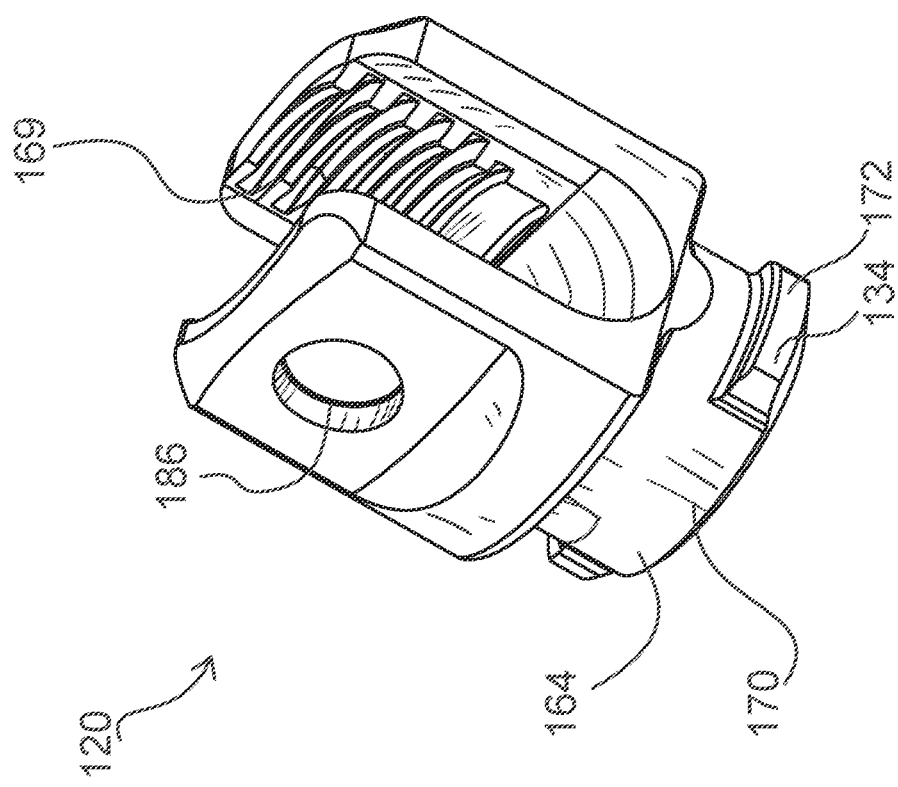
FIG. 17
FIG. 16

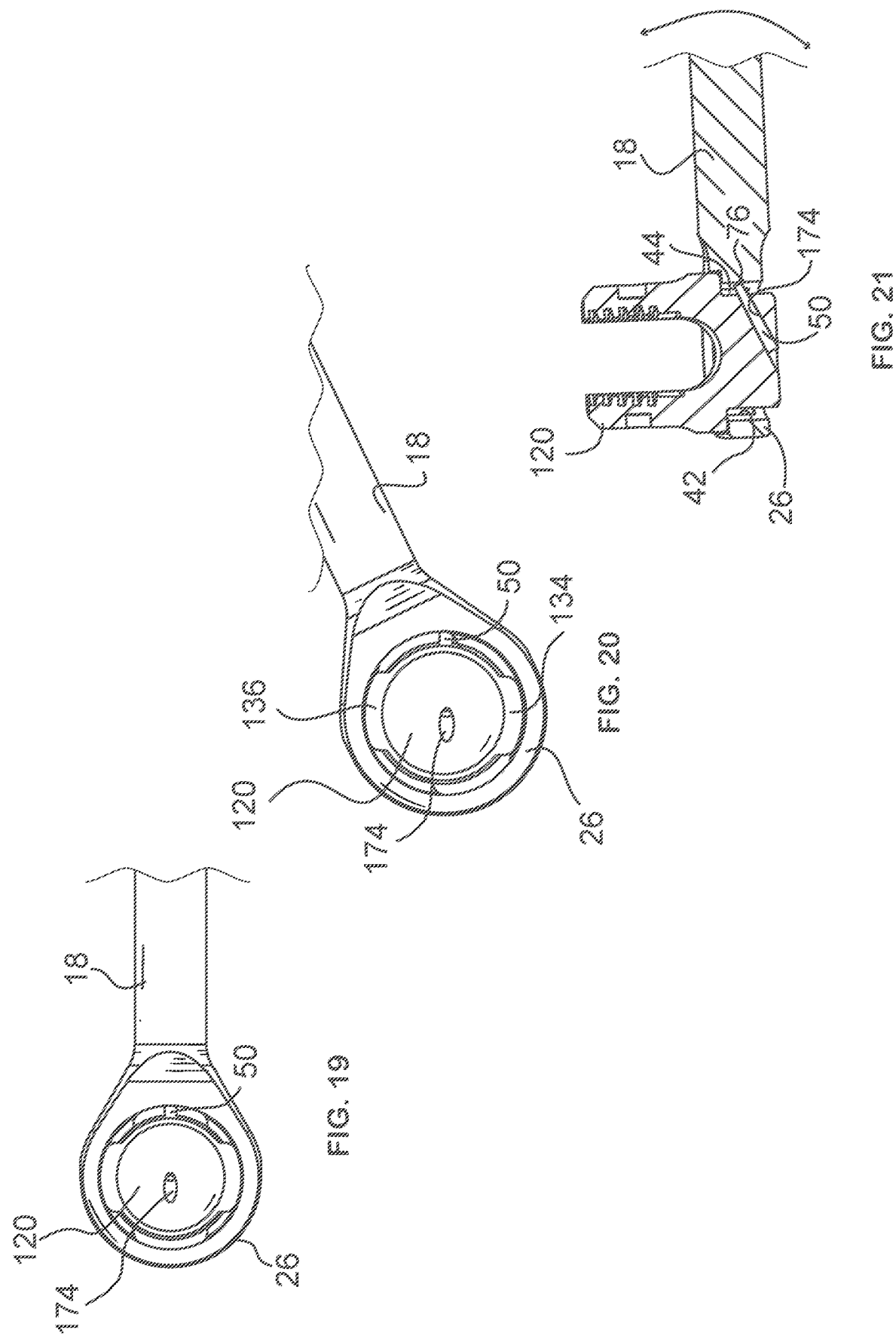

SPINAL IMPLANT AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and support the vertebral members. During surgical treatment, one or more rods and bone fasteners can be delivered to a surgical site. The rods may be attached via the fasteners to the exterior of two or more vertebral members and/or iliac surfaces. This disclosure describes an improvement over these prior technologies.

SUMMARY

In one embodiment, a spinal implant is provided. The spinal implant includes a post with a receiver having a first mating surface and a stop. A connector defines an implant cavity. The connector includes a base having a second mating surface being positionable with the first mating surface to attach the connector with the receiver. The base defines a transverse passageway. A securing element is disposable in the passageway and engageable with the stop. In some embodiments, systems, surgical instruments, implants and methods are disclosed.

In one embodiment, the spinal implant includes a post with a receiver having at least one inner tab and a stop. A connector defines an implant cavity. The connector includes a base having at least one outer tab being positionable with the at least one inner tab to attach the connector with the receiver. The base defines a transverse passageway. A wire is disposable in the passageway and engageable with the stop. The connector is rotatable relative to the receiver to a selected coronal angular orientation to receive a spinal rod.

In one embodiment, a spinal implant system is provided. The spinal implant system includes a spinal implant with a post including a receiver having at least one inner tab and a stop. A connector defines an implant cavity. The connector includes a base having at least one outer tab being positionable with the at least one inner tab to attach the connector with the receiver. The base defines a transverse passageway. A securing element is disposable in the passageway and engageable with the stop. A spinal rod is engageable with the spinal implant.

BRIEF DESCRIPTION OF THE DRAWINGS

FIG. 5 is a cross section view of the components shown in FIG. 3;

FIG. 16 is a perspective view of components of the system shown in FIG. 14;

FIG. 17 is a plan view of the components shown in FIG. 16;

FIG. 19 is a plan view of components of the system shown in FIG. 14;

FIG. 20 is a plan view of components of the system shown in FIG. 14; and

FIG. 21 is a cross section view of components of the system shown in FIG. 14.

DETAILED DESCRIPTION

Figure 1:
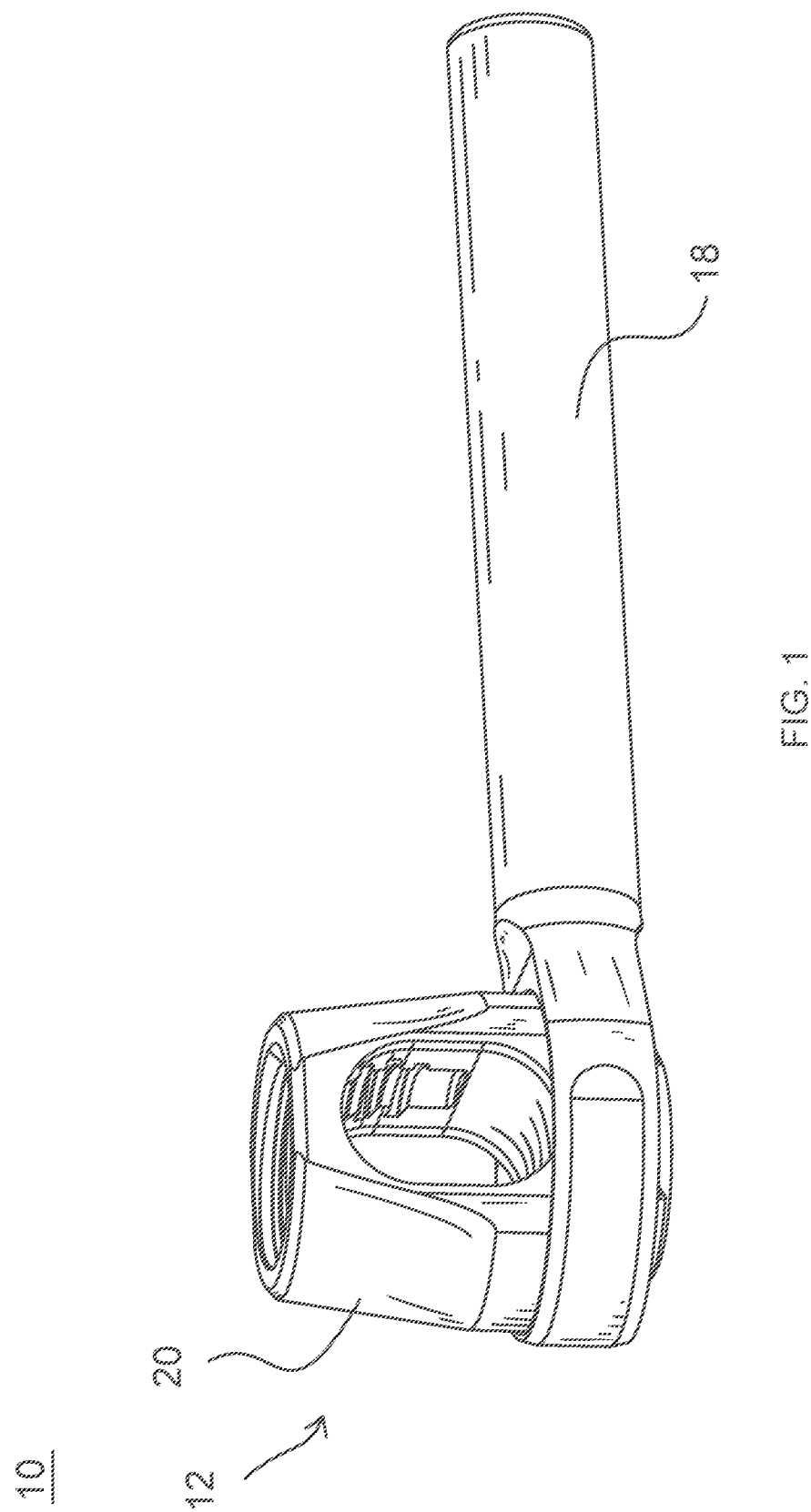
FIG. 1 is a perspective view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a spinal implant system and method for treatment of a spine disorder. In some embodiments, the spinal implant system includes a spinal implant, for example, a post including a receiver and a connector configured for connection with a spinal implant, for example, a spinal rod to facilitate connection of the spinal rod to a bone fastener, for example, an Iliac screw. In some embodiments, the spinal implant system provides stability to a portion of anatomy of a patient, for example, vertebrae, a sacroiliac (SI) joint, and/or iliac bone, and maintains structural integrity while reducing stress on the SI joint and/or portions of the anatomy adjacent the SI joint.

In some embodiments, the present spinal implant system has a spinal implant including a lateral connector and a post that facilitate connection with a bone fastener disposed with vertebrae, an SI joint and/or iliac bone for use in spinal deformity procedures. In some embodiments, the spinal implant can articulate in a coronal plane of a body to facilitate connection to one or more Iliac screws. In some embodiments, the spinal implant articulates in a coronal plane to facilitate connection of an Iliac screw with a spinal implant, for example, a spinal rod. In some embodiments, the spinal implant includes a closed connector configured for connection with a lateral offset post. In some embodiments, the spinal implant includes a top load or an open connector configured for connection with a lateral offset post.

In some embodiments, the present spinal implant system has a spinal implant including a lateral connector and a post having a receiver. In some embodiments, the receiver includes a mating surface that defines one or more tabs and one or more openings. In some embodiments, the connector includes a mating surface that defines one or more tabs. In some embodiments the tab connection is configured to secure the connector with the receiver. In some embodiments, the one or more tabs of the connector are configured for a removable orientation and an attached orientation with the one or more tabs of the receiver. In some embodiments, the one or more tabs of the connector and the one or more tabs of the receiver are configured for alignment in the attached orientation and are disposed out of alignment in the removable orientation relative to each other. In some embodiments, in the attached orientation, the one or more tabs of the connector and receiver are in an interference orientation to provide a rigid attachment between the connector and the receiver. In some embodiments, in the removable orientation, the connector is configured to disengage from the receiver when the one or more tabs are aligned with the one or more openings of the receiver. In some embodiments, the one or more openings of the receiver alternatively include one or more keyways. In some embodiments, the one or more tabs of the connector alternatively include one or more keys. In some embodiments, the one or more tabs of the connector and the one or more tabs of the receiver alternatively include one or more flanges.

In some embodiments, the present spinal implant system has a spinal implant including a lateral connector, a post and a securing element. In some embodiments, the securing element is configured to join the receiver and the connector together. In some embodiments, the securing element includes a wire. In some embodiments, the connector includes a surface that defines a hole and a passageway that is configured for insertion of the wire. In some embodiments, the wire is inserted into the passageway to set an angulation limit and join the connector with the receiver. In some embodiments, the passageway is defined from a bottom of an end of the connector. In some embodiments, a cross section of the receiver of the post is less than a cross section of the connector. In some embodiments, the passageway is in the bottom of the connector to maintain structural integrity of a sidewall of the post. In some embodiments, a material cross section of the end of the connector is greater than a cross section of the receiver. In some embodiments, an end of the wire is configured to prevent the one or more tabs of the connector from moving out of alignment with the one or more tabs of the receiver, thereby preventing disassembly of the connector and the receiver. In some embodiments, sidewalls of the one or more tabs of the receiver maintain, interfere, or otherwise contact the end of the wire to maintain connection of the connector and the receiver.

In some embodiments, the spinal implant of the present spinal implant system can be modular such that the post is configured to be interchangeable with one or more alternately configured connectors, for example a closed and/or a top loaded or open connector. In some embodiments, the spinal implant includes varying post lengths, post diameters and/or is made from the same or different materials. In some embodiments, the post can have a selected length to accommodate a selected anatomy and/or surgical procedure. In some embodiments, the post can be selectively cut before or during a procedure to customize the length of the post to a surgical site.

In some embodiments, the present spinal implant system has a spinal implant including a post and a lateral connector, the post being pivotable relative to the connector. In some embodiments, the post is pivotable relative to the connector in a range of about +/−15 degrees. In some embodiments, the post is pivotable relative to the connector in a coronal plane of a body of a patient. In some embodiments, the post includes +/−25 degrees of rotation relative to the connector. In some embodiments, the connector is configured to rotate 90 degrees relative to the post. In some embodiments, the connector includes a closed lateral connector or a top loaded or an open lateral connector. In some embodiments, the connector includes a similar or identical profile above a rod at a sacral region as existing lateral connectors to dispose a substantial portion of the connector material anterior to a spinal rod to minimize a profile of the spinal implant system posterior to the spinal rod. In some embodiments, the present spinal implant system includes bone fasteners, including multi-axial Iliac screws. In some embodiments, the multi-axial Iliac screws include a low profile to reduce Iliac pain in a patient. In some embodiments, the multi-axial iliac screws include about a 3 mm reduced profile relative to standard multi-axial screws.

In some embodiments, one or all of the components of the spinal implant system may be disposable, peel-pack, prepacked sterile devices. One or all of the components of the spinal implant system may be reusable. The spinal implant system may be configured as a kit with multiple sized and configured components.

In some embodiments, the spinal implant system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the spinal implant system of the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The spinal implant system of the present disclosure may also be alternatively employed with procedures for treating the lumbar, cervical, thoracic, sacral and pelvic regions of a spinal column. The spinal implant system of the present disclosure may also be used on animals, bone models and other non-living substrates, for example, in training, testing and demonstration.

The spinal implant system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal implant, related components and methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-21, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, spinal implant system 10 is configured for use in deformity correction procedures including spondylolisthesis, kyphosis and scoliosis correction procedures. In some embodiments, one or more of the components of spinal implant system 10 are configured for engagement with existing spinal constructs, which may include fastener implants and/or spinal rod implants attached with vertebrae, in a revision surgery to manipulate tissue and/or correct a spinal disorder, as described herein.

Spinal implant system 10 includes a spinal implant 12 configured for connection with a spinal rod 14 to facilitate connection of spinal rod 14 to a bone fastener, for example, an Iliac screw 16, as shown in FIGS. 1-11. Spinal implant system 10 provides stability to a portion of anatomy of a patient, for example, vertebrae, an SI joint, and/or iliac bone, and maintains structural integrity while reducing stress on the SI joint and/or portions of the anatomy adjacent the SI joint.

Figure 2:
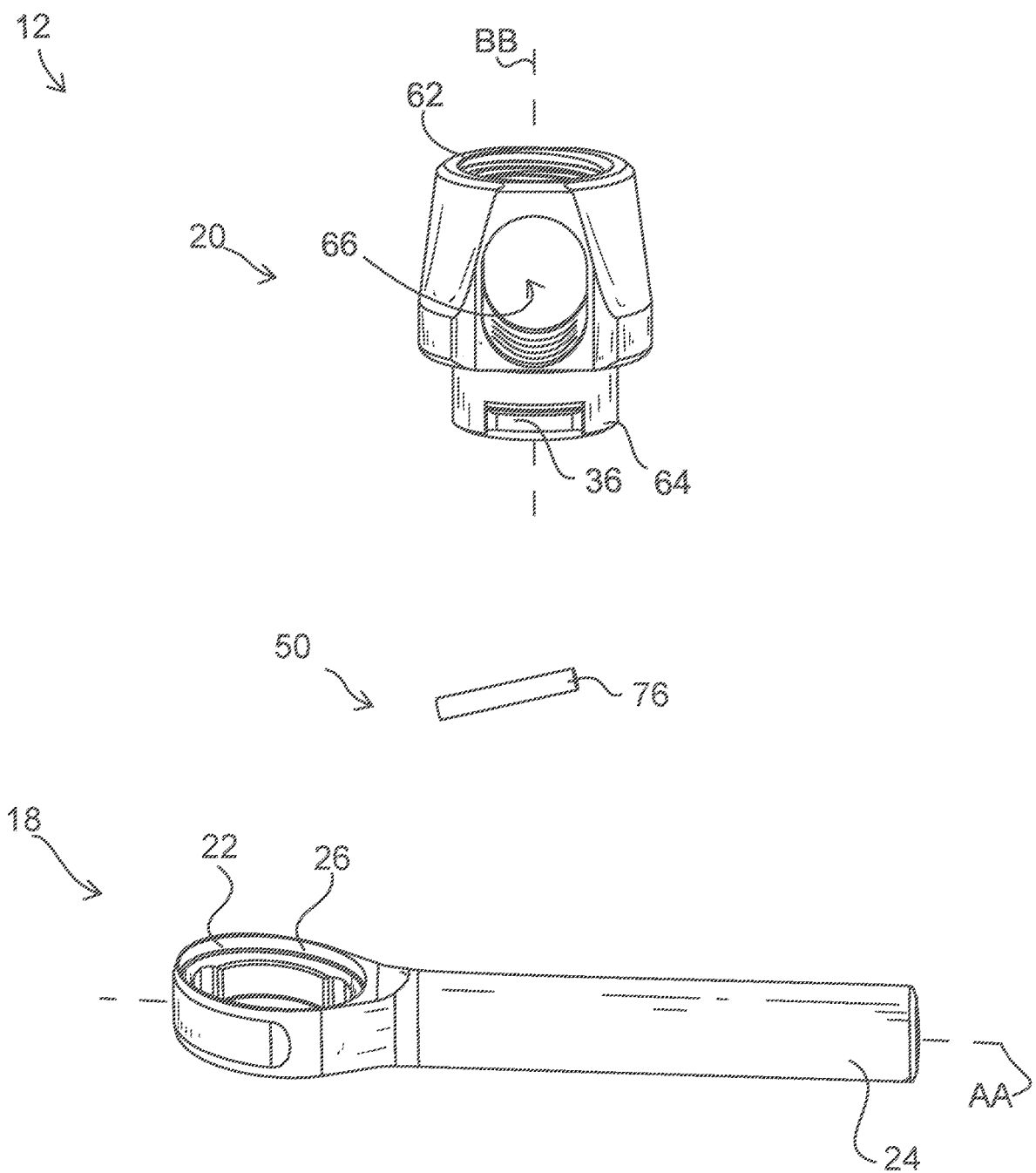
FIG. 2 is a perspective view of the components shown in FIG. 1 with parts separated.

Spinal implant 12 is configured for attachment to vertebrae, sacral and/or iliac bone, and for articulation of one or more components of spinal implant 12 in a plane, for example, a coronal plane of a body of a patient. Spinal implant 12 includes a post 18 configured for attachment with a connector 20, as shown in FIG. 1. Post 18 extends between an end 22 and an end 24, and post 18 defines a longitudinal axis AA, as shown in FIG. 2. End 22 includes a receiver 26 configured for engagement with connector 20. End 22 includes a circular configuration.

Figure 6:
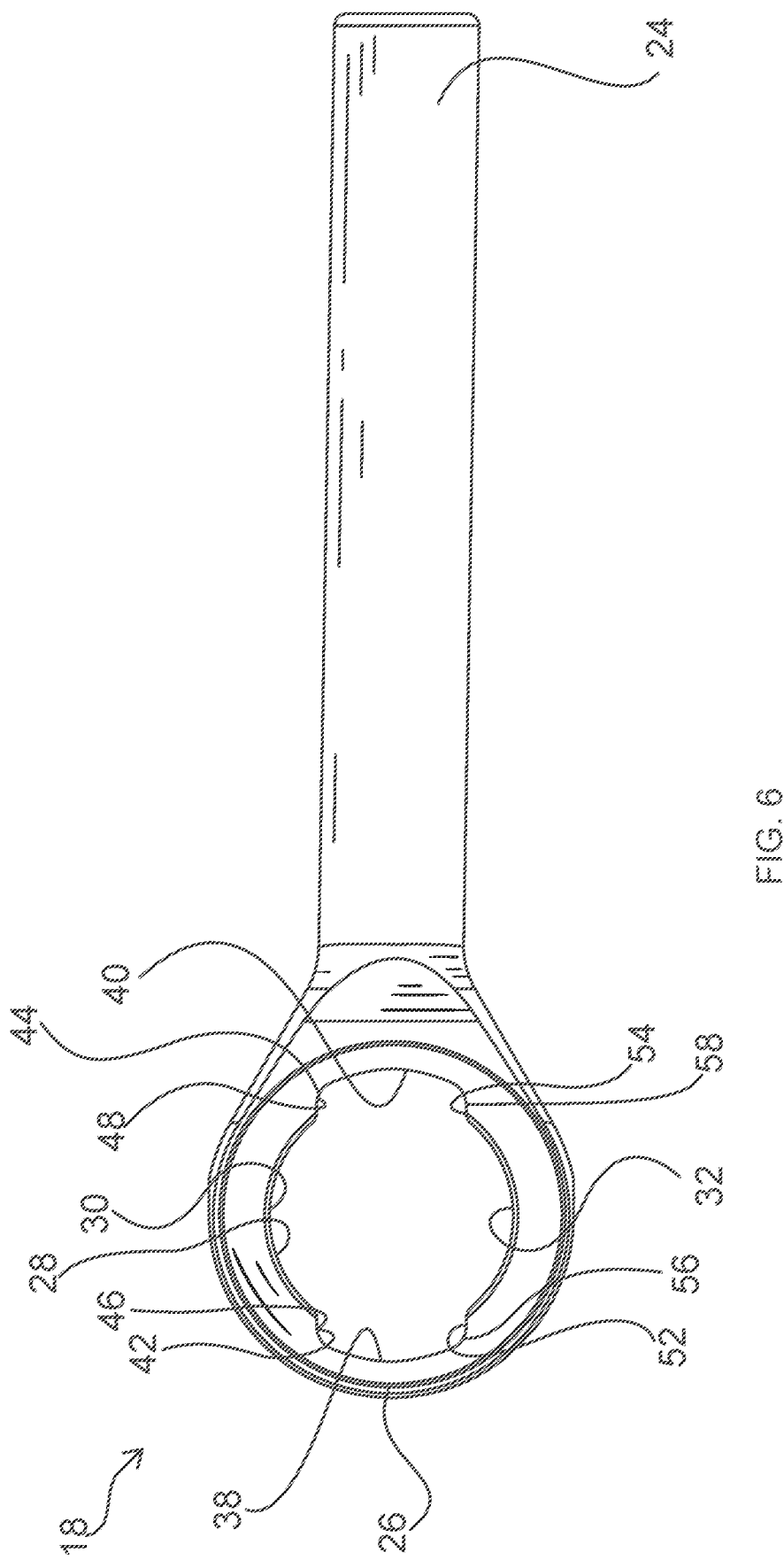
FIG. 6 is a plan view of components of the system shown in FIG. 1.
Figure 7:
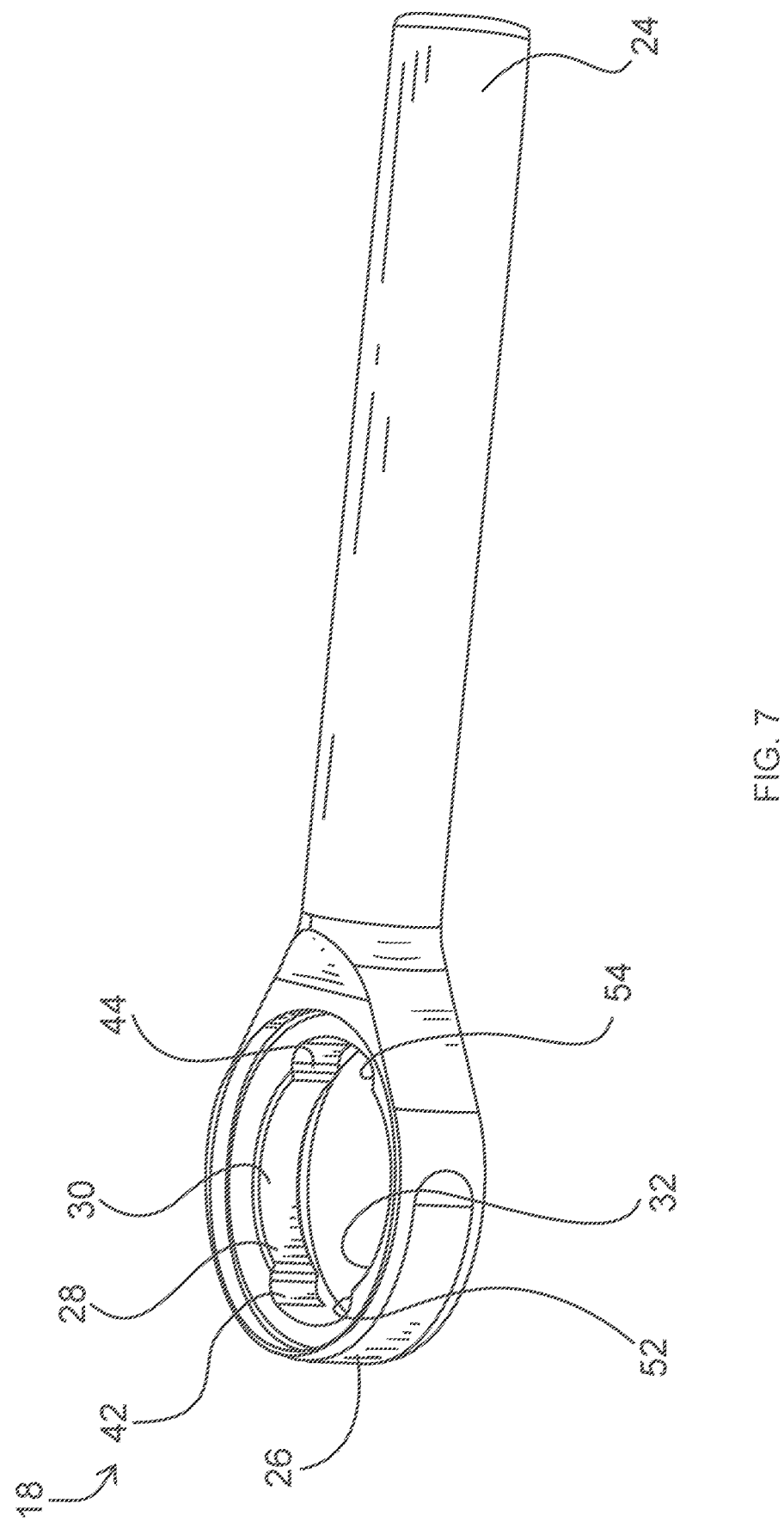
FIG. 7 is a perspective view of the components shown in FIG. 6.

Receiver 26 includes an inner surface defining a mating surface 28, as shown in FIGS. 6 and 7. Mating surface 28 includes at least one inwardly projecting surface, for example, inner tabs 30, 32. Tabs 30, 32 are configured for engagement with outwardly projecting tabs 34, 36 of connector 20, such that tabs 34, 36 are movable relative to receiver 26 between a removable orientation and an attached orientation, as described herein.

The inner surface of receiver 26 defines openings 38, 40. Tab 30 is spaced apart from tab 32 via openings 38, 40. Openings 38, 40 are configured for alignment with tabs 34, 36 of connector 20 in the removable orientation, as described herein. Tab 30 includes a sidewall 42 and a sidewall 44. Sidewall 42 includes a stop 46 and sidewall 44 includes a stop 48. Stops 46, 48 are engageable with a securing element, for example, a wire 50, as described herein and shown in FIG. 8. Stops 46, 48 are configured to prevent rotation of connector 20 when attached to receiver 26. Sidewalls 42, 44 are angled and have a lead-in or ramp configuration. Tab 32 includes a sidewall 52 and a sidewall 54. Sidewall 52 includes a stop 56 and sidewall 54 includes a stop 58. Stops 56, 58 are engageable with wire 50. Stops 56, 58 are configured to prevent rotation of connector 20 when attached to receiver 26. Sidewalls 52, 54 are angled and have a lead-in or ramp configuration.

End 24 of post 18 is configured for engagement with a portion of iliac screw 16 or an iliac screw 17, as shown in FIGS. 2 and 11-13. End 24 includes a cylindrical configuration.

In some embodiments, end 22 of post 18 may be variously configured and dimensioned, for example, oval, oblong, square, rectangular, polygonal, irregular, uniform, non-uniform, offset, staggered, tapered, consistent and/or variable. In some embodiments, tabs 30, 32 may be variously configured and dimensioned, for example, oval, oblong, square, rectangular, polygonal, irregular, uniform, non-uniform, offset, staggered, tapered, consistent and/or variable. In some embodiments, tabs 30, 32 may alternatively include flanges, splines, ledges and/or projections. In some embodiments, all or a portion of tabs 30, 32 may be circumferential. In some embodiments, mating surface 28 may have alternate surface configurations, for example, rough, arcuate, undulating, porous, semi-porous, dimpled, polished and/or textured. In some embodiments, all or a portion of openings 38, 40 may be variously configured and dimensioned, for example, oval, oblong, square, rectangular, polygonal, irregular, uniform, non-uniform, offset, staggered, tapered, consistent and/or variable. In some embodiments, openings 38, 40 may alternatively include keyways. In some embodiments, sidewalls 42, 44 and sidewalls 52, 54 may be variously configured and dimensioned, for example irregular, uniform, non-uniform, offset, staggered, tapered, consistent and/or variable.

In some embodiments, end 24 of post 18 may have alternate cross section configurations, for example, cylindrical, oval, oblong, triangular, square, polygonal, irregular, uniform, non-uniform, offset, staggered, undulating, arcuate, variable and/or tapered. In some embodiments, end 24 may have alternate surface configurations, for example, smooth, rough, arcuate, undulating, mesh, porous, semi-porous, dimpled and/or textured.

Connector 20 includes a closed connector, as shown in FIG. 1. Connector 20 is rotatable relative to receiver 26 to a selected angular orientation to receive spinal rod 14, as shown in FIGS. 9 and 11-13. Connector 20 extends between an end 62 and an end 64, and connector 20 defines a longitudinal axis BB, as shown in FIG. 2. Longitudinal axis AA is disposed perpendicular relative to longitudinal axis BB. Connector 20 defines an implant cavity 66 configured for engagement with spinal rod 14. An inner surface includes a plurality of threads 68 configured for engagement with a setscrew (not shown) such that when spinal rod 14 is received by connector 20, spinal rod 14 can be fixed with connector 20 via the set screw.

Figure 4:
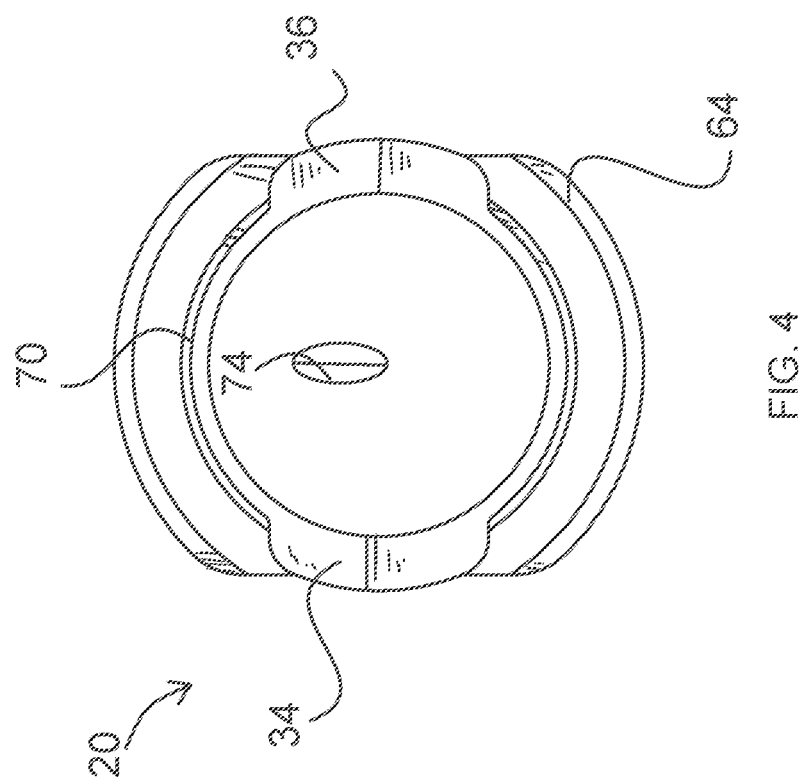
FIG. 4 is a plan view of the components shown in FIG. 3.
Figure 3:
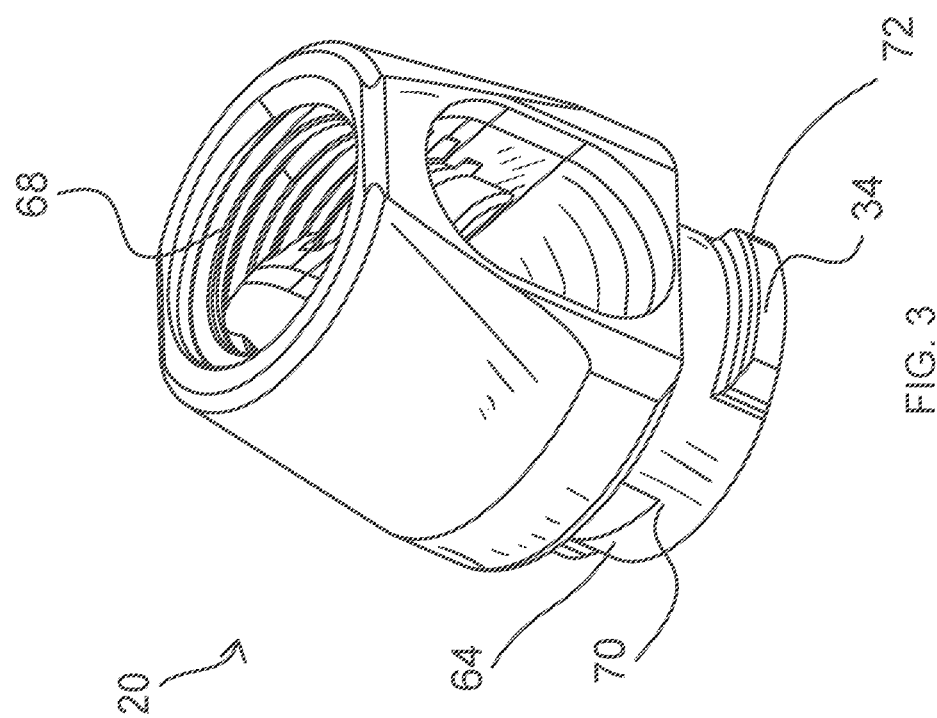
FIG. 3 is a perspective view of components of the system shown in FIG. 1.
Figure 8:
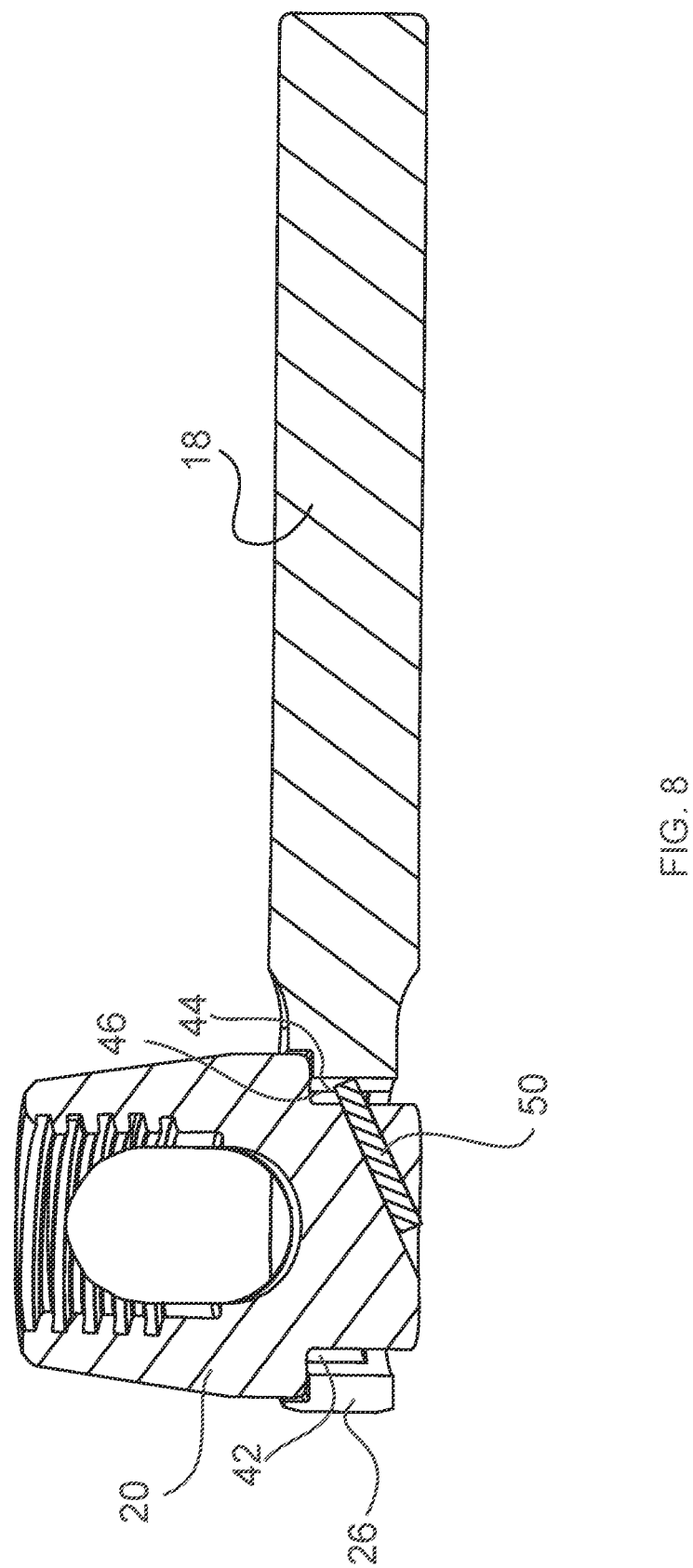
FIG. 8 is a cross section view of the components shown in FIG. 1.
Figure 9:
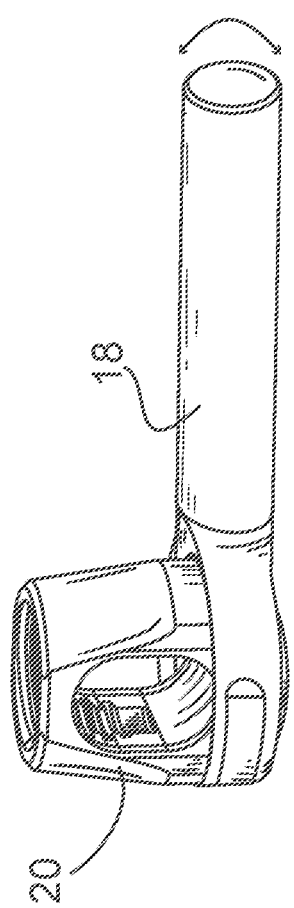
FIG. 9 is a perspective view of the components shown in FIG. 1.

End 64 of connector 20 includes a base 70, as shown in FIGS. 3 and 4. Base 70 includes an outer surface that defines a mating surface 72. Mating surface 72 is positionable with mating surface 28 to attach connector 20 with receiver 26. Mating surface 72 includes at least one outwardly projecting surface, for example, outer tabs 34, 36, described herein. Tabs 34, 36 are configured for engagement with tabs 30, 32 of receiver 26 such that tabs 34, 36 are movable relative to receiver 26 between the removable orientation and the attached orientation. Tabs 34, 36 are rotatable relative to tabs 30, 32 of receiver 26 for alignment in an interference orientation, as shown in FIGS. 8 and 9.

In the removable orientation, tabs 34, 36 of connector 20 are disposed out of alignment with tabs 30, 32 of receiver 26 and tabs 34, 36 are aligned with openings 38, 40 of receiver 26 such that connector 20 can be removed from receiver 26. In the attached orientation, tabs 34, 36 are aligned and engage with tabs 30, 32 such that connector 20 is attached to receiver 26. In the attached orientation, tabs 30, 32 are aligned with tabs 34, 36 and disposed in an interference orientation.

An inner surface of base 70 defines a passageway 74, as shown in FIG. 5. Passageway 74 is transverse relative to connector 20. Wire 50 is configured for disposal within passageway 74, and an end 76 of wire 50 is engageable with stops 46, 48, 56 and 58 to join connector 20 with receiver 26. Wire 50 is configured for slidable engagement with the inner surface that defines passageway 74. In some embodiments, wire 50 is configured for engagement with the inner surface of passageway 74 in a friction fit. Passageway 74 extends from a distal facing opening 78 to a lateral opening 80, and passageway 74 defines a longitudinal axis CC. Longitudinal axis CC is transverse relative to longitudinal axis BB. Passageway 74 is angled relative to longitudinal axis BB and longitudinal axis AA. In some embodiments, wire 50 is welded to a surface of opening 78. In some embodiments, wire 50 is retained within passageway 74 via staking or deforming a surface of opening 78.

Figure 10:
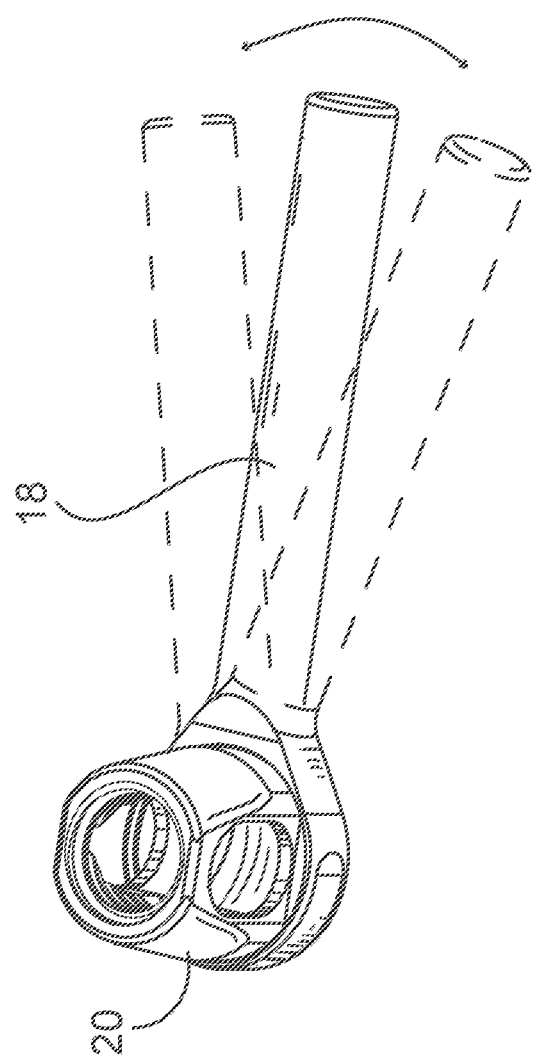
FIG. 10 a perspective view of the components shown in FIG. 1.

In some embodiments, post 18 includes +/−25 degrees of rotation relative to connector 20. In some embodiments, connector 20 is configured to rotate 90 degrees relative to post 18 and/or receiver 26. In some embodiments, post 18 is pivotable relative to connector 20 in a range of +/−15 degrees, as shown in FIG. 10. In some embodiments, post 18 is pivotable relative to connector 20 relative to a coronal plane of a body of a patient.

In some embodiments, connector 20 may be coupled with receiver 26 in alternate fixation configurations, for example, friction fit, pressure fit, locking protrusion/recess, locking keyway and/or adhesive. In some embodiments, connector 20 may be disposed with receiver 26 for relative movement thereto, for example, transverse, perpendicular and/or other angular orientations including acute or obtuse, co-axial and/or may be offset or staggered. In some embodiments, connector 20 may move relative to receiver 26 in alternate planes relative to a body, for example, transverse and/or sagittal planes of a body.

In some embodiments, tabs 34, 36 may be variously configured and dimensioned, for example, oval, oblong, square, rectangular, polygonal, irregular, uniform, non-uniform, offset, staggered, tapered, consistent and/or variable. In some embodiments, tabs 34, 36 may alternatively include flanges, keys, splines, ledges and/or projections. In some embodiments, all or a portion of tabs 34, 36 may be circumferential. In some embodiments, mating surface 72 may have alternate surface configurations, for example, rough, arcuate, undulating, porous, semi-porous, dimpled, polished and/or textured.

In some embodiments, passageway 74 may be variously configured and dimensioned, for example, oval, oblong, square, rectangular, polygonal, irregular, uniform, non-uniform, offset, staggered, tapered, consistent and/or variable. In some embodiments, passageway 74 may be disposed at alternate orientations, relative to longitudinal axis BB and/or longitudinal axis CC, for example, perpendicular and/or other angular orientations including acute or obtuse, coaxial and/or may be offset or staggered.

In some embodiments, spinal implant 12 may be disposed with iliac screw 16 and/or spinal rod 14 for relative movement thereto in orientations relative to iliac screw 16 and/or spinal rod 14, for example, transverse, perpendicular and/or other angular orientations including acute or obtuse, co-axial and/or may be offset or staggered. In some embodiments, spinal implant 12 may move relative to iliac screw 16 and/or spinal rod 14 in alternate planes relative to the body, for example, transverse and/or sagittal planes of a body.

In assembly, operation and use, spinal implant system 10, including spinal implant 12, spinal rod 14 and iliac screw 16 or iliac screw 17, similar to that described above with regard to FIGS. 1-13 is employed with a surgical procedure for treatment of a spinal disorder affecting a section of a spine, including vertebrae V, the sacrum S, ilium I bones of a pelvis and/or a sacroiliac SI joint of a patient, as shown in FIGS. 11-13. Spinal implant system 10 may also be employed with other surgical procedures. In some embodiments, spinal implant system 10 is attached to vertebrae V, sacrum S, ilium I and/or an SI joint for a deformity correction procedure, including spondylolisthesis, kyphosis and/or scoliosis correction procedures.

In use, to treat the affected section of the spine, a medical practitioner obtains access to a surgical site including vertebrae V, the sacrum S, the ilium I, and/or the SI joint in any appropriate manner, such as through incision and retraction of tissues. In some embodiments, spinal implant system 10 may be used in any existing surgical method or technique including open surgery, mini-open surgery, minimally invasive surgery and percutaneous surgical implantation, whereby vertebrae V, sacrum S, ilium I, and/or the SI joint is accessed through a micro-incision, or sleeve that provides a protected passageway to the area. Once access to the surgical site is obtained, the particular surgical procedure is performed for treating the bone disorder. Spinal implant system 10 is then employed to augment the surgical treatment. In some embodiments, spinal implant system 10 can be delivered or implanted as a pre-assembled device or can be assembled in situ. Spinal implant system 10 may be completely or partially revised, removed or replaced.

Figure 11:
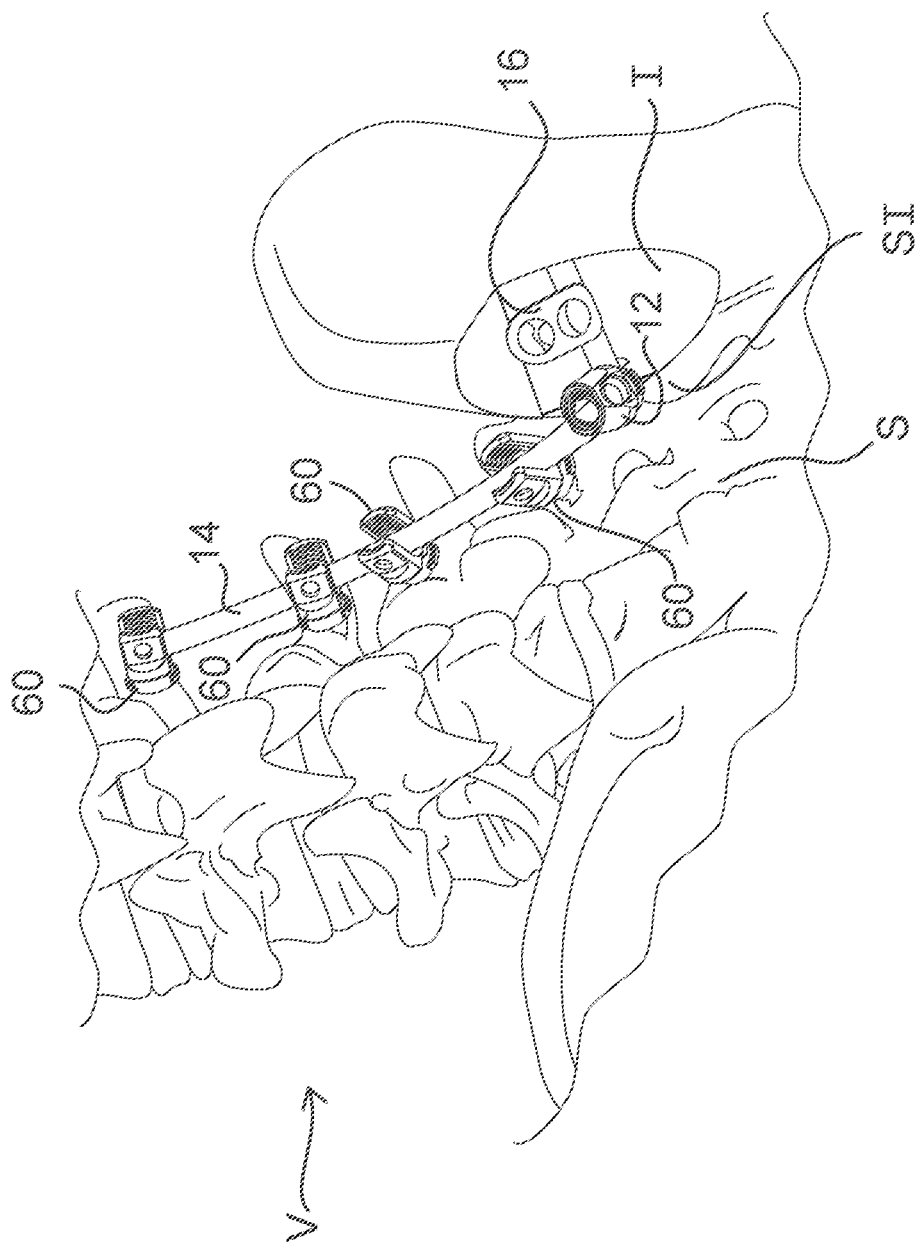
FIG. 11 is a perspective view of components of one embodiment of a spinal implant system in accordance with the principles of the present disclosure disposed with patient anatomy.

Pilot holes are made within a portion of the ilium I, a portion of the sacrum S, and portions of vertebrae V, for receiving iliac screw 16 or bone screws 60. Spinal rod 14 is disposed with bone screws 60. End 24 of post 18 is attached with iliac screw 16, as shown in FIG. 11, and receiver 26 of post 18 is attached with connector 20 in an assembled configuration. In some embodiments, end 24 of post 18 is attached with bone fastener 17, as shown in FIGS. 12-13.

Figure 13:
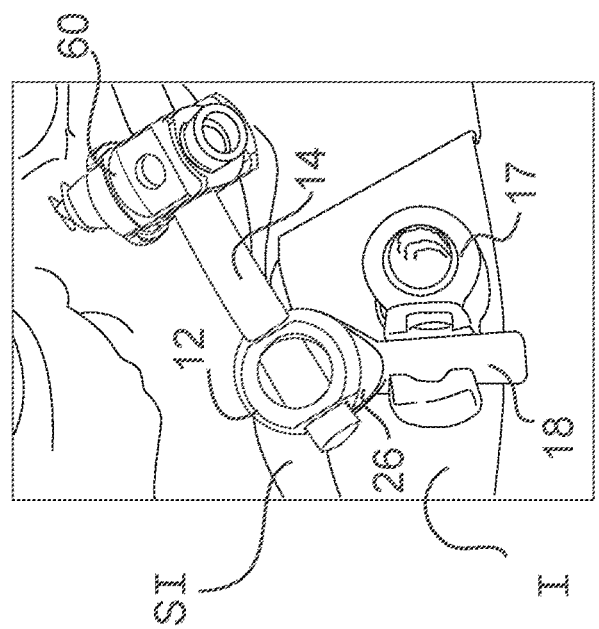
FIG. 13 is a break away view of components of the system shown in FIG. 12 disposed with patient anatomy.
Figure 12:
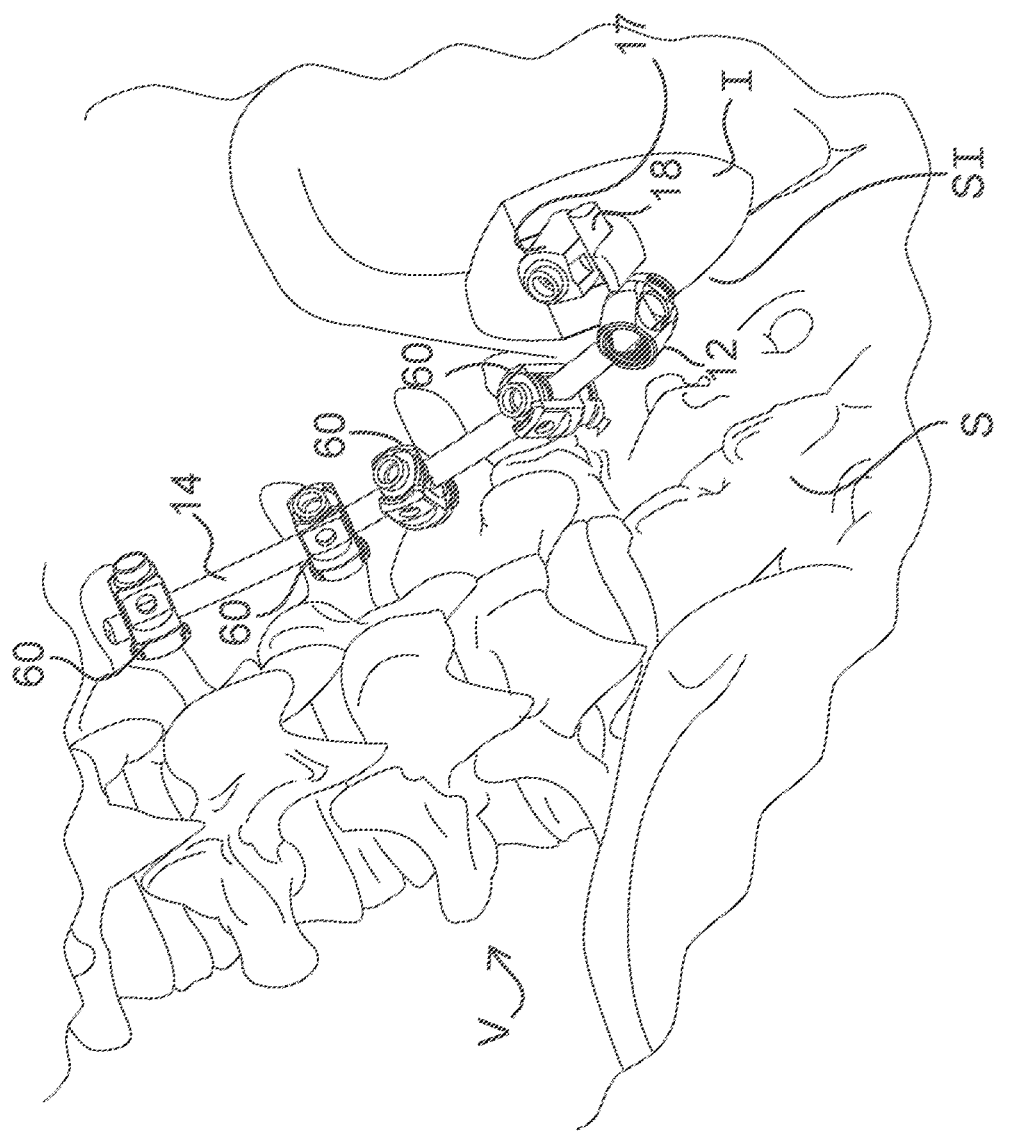
FIG. 12 is a perspective view of components of one embodiment of a spinal implant system in accordance with the principles of the present disclosure disposed with patient anatomy.

Connector 20 is rotatable relative to receiver 26 to a selected angular orientation to receive spinal rod 14, as shown in FIGS. 11-13. A setscrew (not shown) may be threaded with threads 68 of connector 20 to fix spinal rod 14 with connector 20. In some embodiments, connector 20 is configured to rotate 90 degrees relative to receiver 26. In some embodiments, post 18 is pivotable relative to connector 20 in a range of +/−15 degrees. In some embodiments, post 18 is pivotable relative to a coronal plane of a body of the patient.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In one embodiment, shown in FIGS. 14-21, spinal implant system 10, similar to the systems and methods described herein, includes a spinal implant 112, similar to spinal implant 12. Spinal implant 112 is configured for attachment to vertebrae, for example, iliac bone, and for articulation in a plane, for example, a coronal plane of a body of a patient to connect with iliac screw 16 and spinal rod 14.

Figure 14:
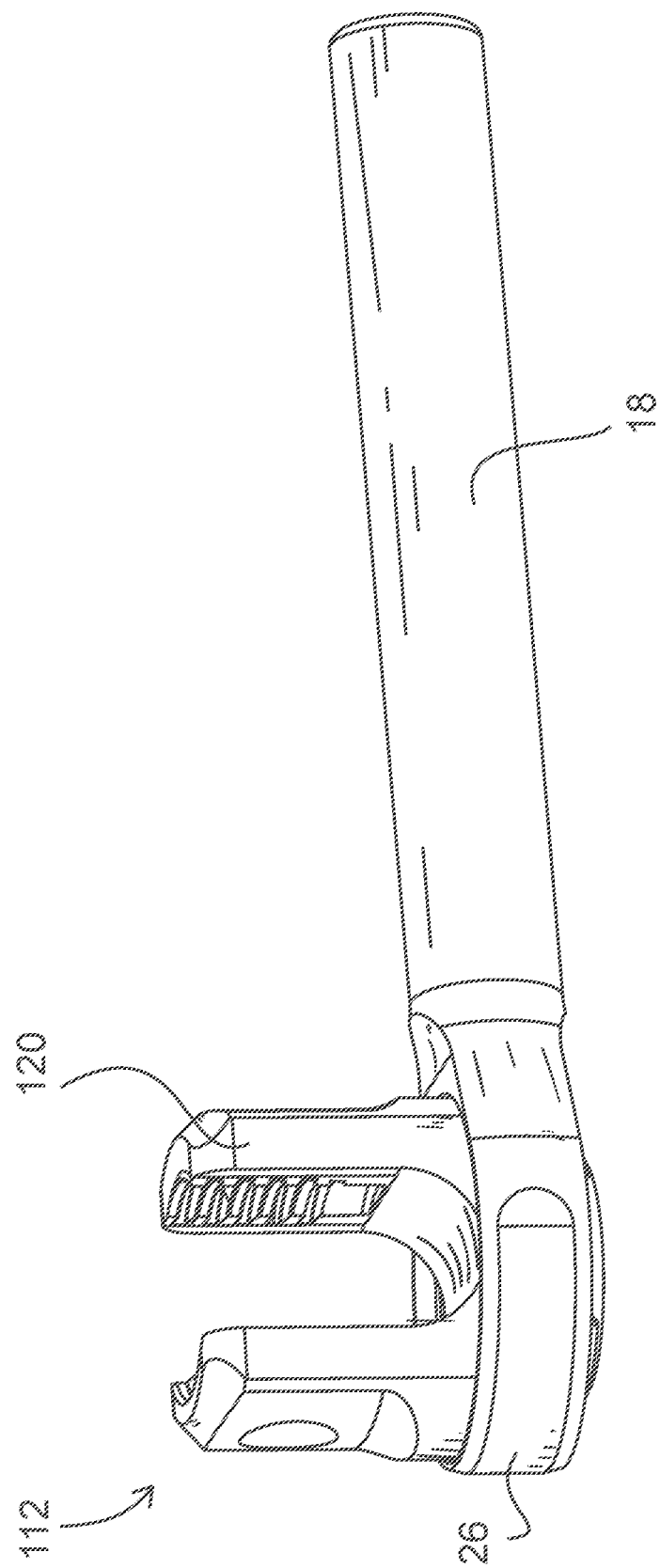
FIG. 14 is a perspective view of components of one embodiment of a spinal implant system in accordance with the principles of the present disclosure.

Spinal implant 112 includes a connector 120, similar to connector 20 and post 18 including receiver 26 configured for engagement with connector 120, as shown in FIG. 14. Connector 120 is configured for attachment with post 18, as described herein. Connector 120 includes an open or top loaded connector. Connector 120 is rotatable relative to receiver 26 to a selected angular orientation to receive spinal rod 14.

Figure 15:
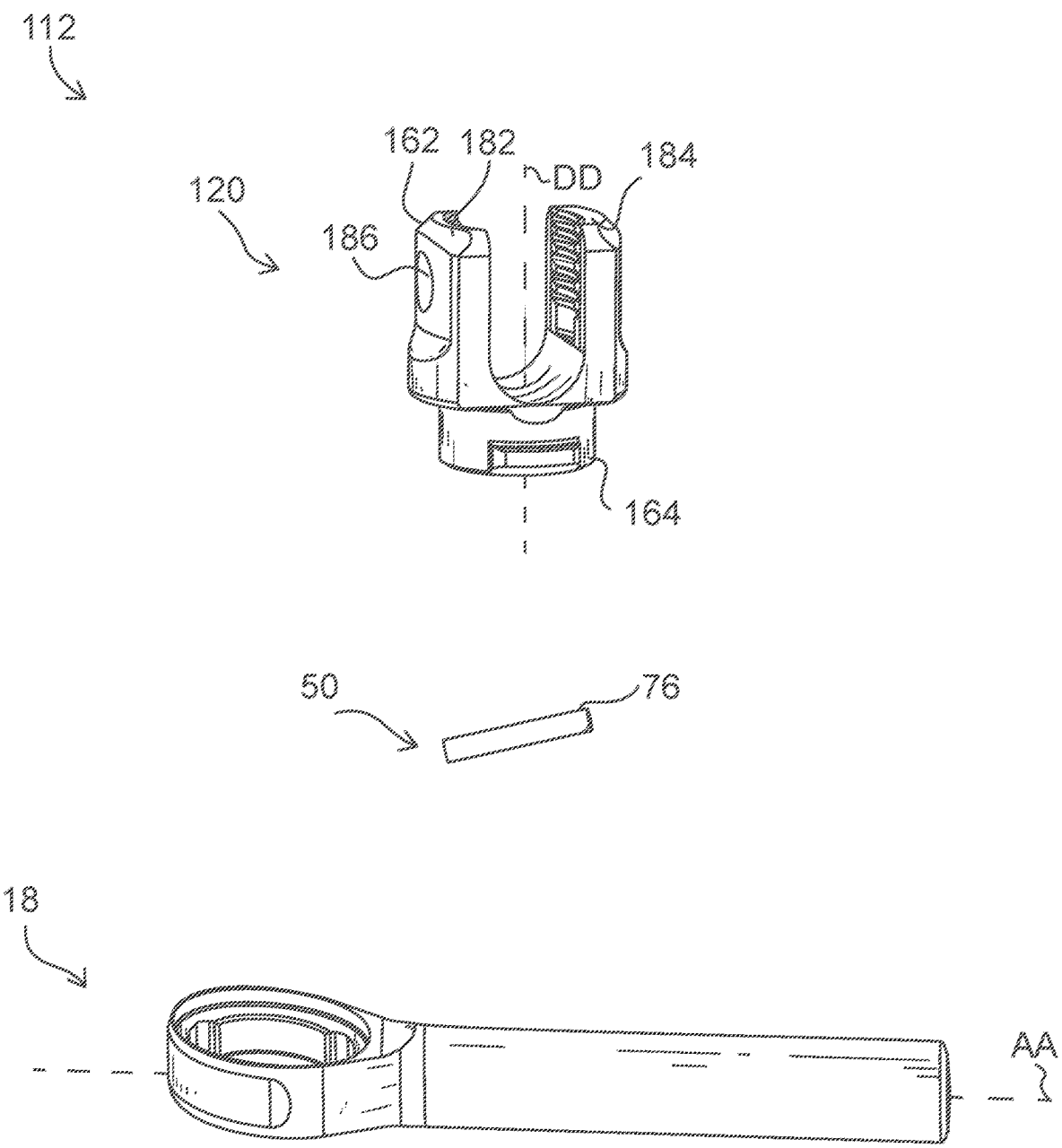
FIG. 15 is a perspective view of the components shown in FIG. 14 with parts separated.
Figure 18:
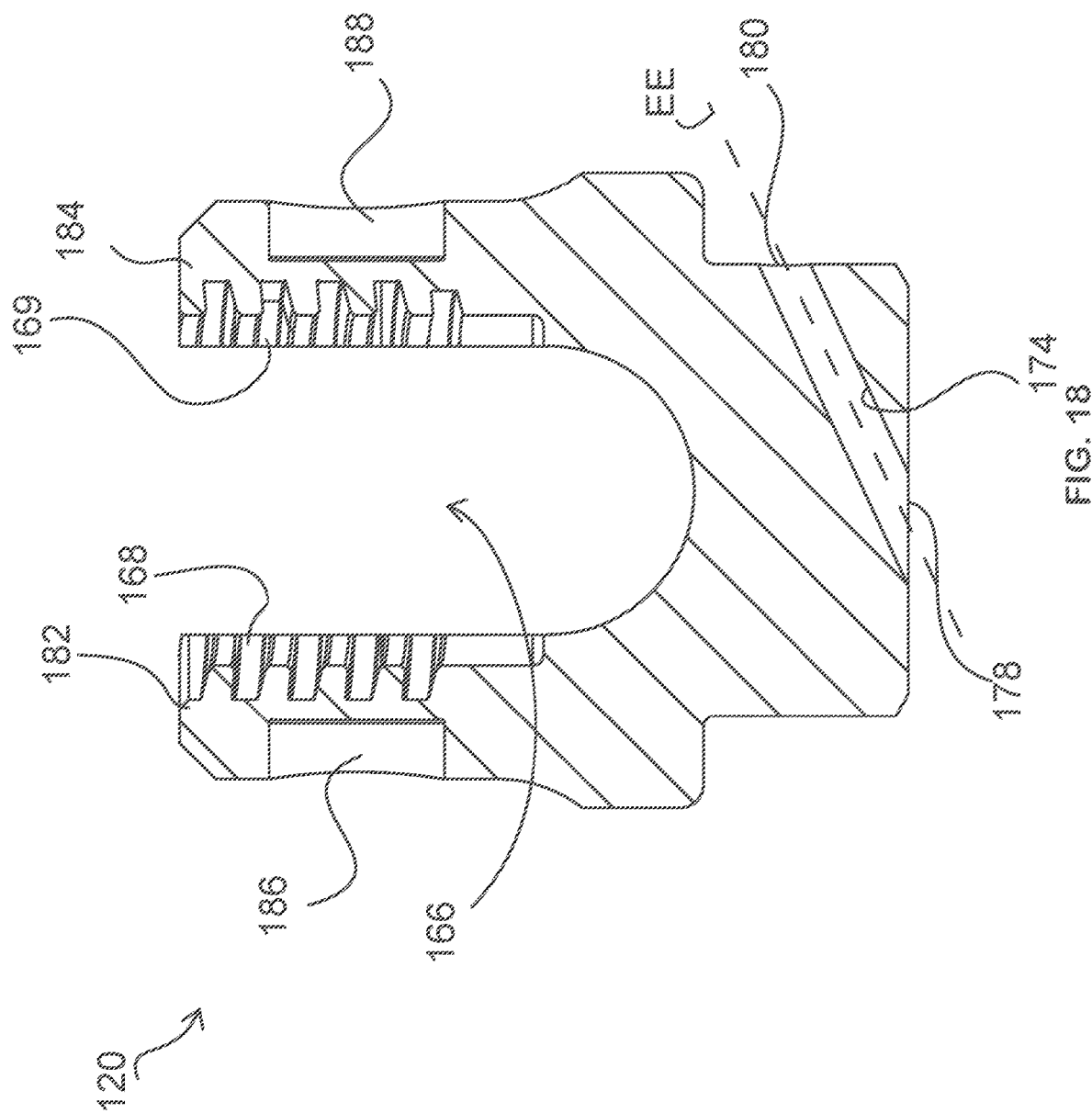
FIG. 18 is a cross section view of the components shown in FIG. 16.

Connector 120 extends between an end 162 and an end 164, and connector 120 defines a longitudinal axis DD, as shown in FIG. 15. Longitudinal axis AA of post 18 is perpendicular relative to longitudinal axis DD. Connector 120 includes an arm 182, and an arm 184 spaced apart from arm 182. Arms 182, 184 each extend parallel to axis DD. Arm 182 includes an arcuate outer surface that defines a recess or cavity 186, and arm 184 includes an arcuate outer surface that defines a recess or cavity 188, as shown in FIG. 18. Recess or cavities 186, 188 are configured to receive an insertion tool, compression instrument and/or surgical instruments for manipulating connector 120 (not shown).

Arms 182, 184 define an implant cavity 166 configured for engagement with spinal rod 14. An inner surface of each arm 182, 184 includes a plurality of threads 168, 169 configured for engagement with a setscrew (not shown) such that when spinal rod 14 is received by connector 120, spinal rod 14 can be fixed with connector 120 via the set screw.

End 164 of connector 120 includes a base 170, as shown in FIGS. 16 and 17. Base 170 includes an outer surface that defines mating surface 172. Mating surface 172 is positionable with mating surface 28 of receiver 26 to attach connector 120 with receiver 26. Mating surface 172 includes at least one outwardly projecting surface, for example, outer tabs 134, 136, described herein. Tabs 134, 136 are configured for engagement with tabs 30, 32 of receiver 26 such that tabs 134, 136 are movable relative to receiver 26 between the removable orientation and the attached orientation, described herein. Tabs 134, 136 are rotatable relative to tabs 30, 32 of receiver 26 for alignment in an interference orientation, as shown in FIGS. 20 and 21.

In the removable orientation, tabs 134, 136 of connector 120 are disposed out of alignment with tabs 30, 32 of receiver 26 and tabs 134, 136 are aligned with openings 38, 40 of receiver 26 such that connector 120 can be removed from receiver 26. In the attached orientation, tabs 134, 136 are aligned and engage with tabs 30, 32 such that connector 120 is attached to receiver 26. In the attached orientation, tabs 30, 32 are aligned with tabs 134, 136 and disposed in an interference orientation.

An inner surface of base 170 defines a passageway 174, as shown in FIGS. 17-21. Passageway 174 is transverse relative to connector 120. Wire 50 is configured for disposal within passageway 174, and end 76 of wire 50 is engageable with stops 46, 48, 56 and 58 of receiver 26 to join connector 120 with receiver 26. Wire 50 is configured for slidable engagement with the inner surface that defines passageway 174. In some embodiments, wire 50 is configured for engagement with the inner surface of passageway 174 in a friction fit. Passageway 174 extends from a distal facing opening 178 to a lateral opening 180, and passageway 174 defines a longitudinal axis EE, as shown in FIG. 18. Longitudinal axis EE is transverse relative to longitudinal axis DD. Passageway 174 is angled relative to longitudinal axis DD and longitudinal axis AA. In some embodiments, wire 50 is welded to a surface of opening 178. In some embodiments, wire 50 is retained within passageway 174 via staking or deforming a surface of opening 178.

In some embodiments, connector 120 may be coupled with receiver 26 in alternate fixation configurations, for example, friction fit, pressure fit, locking protrusion/recess, locking keyway and/or adhesive. In some embodiments, connector 120 may be disposed with receiver 26 for relative movement thereto, for example, transverse, perpendicular and/or other angular orientations including acute or obtuse, co-axial and/or may be offset or staggered. In some embodiments, connector 120 may move relative to receiver 26 in alternate planes relative to a body, for example, transverse and/or sagittal planes of a body.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a post including a receiver having a first mating surface and a stop, the first mating surface including at least one inner tab;
   a connector defining a longitudinal axis and an implant cavity,
   the connector including a base having a second mating surface being positionable with the first mating surface to attach the connector with the receiver, the base including a wall surface that defines a transverse passageway extending from a distal facing opening to a lateral opening, the transverse passageway being isolated from the implant cavity; and
   a securing element disposable in the passageway and engageable with the stop.

2. The spinal implant of claim 1, wherein the at least one inner tab includes at least one inwardly projecting surface.

3. The spinal implant of claim 2, wherein the second mating surface includes at least one outwardly projecting surface.

4. The spinal implant of claim 1, wherein the second mating surface includes at least one outer tab.

5. The spinal implant of claim 1, wherein the at least one inner tab includes a first inner tab and a second inner tab, the tabs being spaced apart.

6. The spinal implant of claim 1, wherein the second mating surface includes at least one outer tab, the at least one outer tab being rotatable relative to the at least one inner tab for alignment in an interference orientation.

7. The spinal implant of claim 1, wherein the second mating surface includes at least one outer tab, the at least one outer tab being movable relative to the receiver between a removable orientation and an attached orientation with the at least one inner tab.

8. The spinal implant of claim 7, wherein the removable orientation includes the at least one outer tab being disposed out of alignment with the at least one inner tab and the attached orientation includes the at least one outer tab being aligned with the at least one inner tab.

9. The spinal implant of claim 7, wherein the at least one inner tab includes a first tab and a second tab defining at least one opening therebetween such that the removable orientation includes the at least one outer tab being aligned with the at least one opening and the attached orientation includes the at least one inner tab being aligned with the at least one outer tab and disposed in an interference orientation.

10. The spinal implant of claim 1, wherein the securing element includes a wire.

11. The spinal implant of claim 10, wherein an end of the wire is configured to engage with a sidewall of the first mating surface to join the connector with the receiver.

12. The spinal implant of claim 10, wherein the wire slidably engages the wall surface to engage with the stop.

13. The spinal implant of claim 1, wherein the connector is rotatable relative to the receiver to a selected angular orientation to receive a spinal rod.

14. The spinal implant of claim 1, wherein the connector is a closed spinal rod receiver.

15. The spinal implant of claim 1, wherein the connector is an open spinal rod receiver.

16. A spinal implant comprising:
    a post including a receiver having at least one inner tab and a stop;
    a connector defining a longitudinal axis and an implant cavity,
    the connector including a base having at least one outer tab being positionable with the at least one inner tab to attach the connector with the receiver, the base including a wall surface that defines a transverse passageway extending from a distal facing opening to a lateral opening, the transverse passageway being isolated from the implant cavity; and a wire disposable in the passageway and engageable with the stop, the connector being rotatable relative to the receiver to a selected coronal angular orientation to receive a spinal rod.

17. The spinal implant of claim 16, wherein the at least one outer tab is rotatable relative to the receiver for alignment with the at least one inner tab in an interference orientation.

18. The spinal implant of claim 16, wherein an end of the wire is configured to engage with a sidewall of the at least one inner tab to join the connector with the receiver.

19. A spinal implant system comprising:

a spinal implant including a post including a receiver having at least one inner tab and a stop, a connector defining a longitudinal axis and an implant cavity, the connector including a base having at least one outer tab being positionable with the at least one inner tab to attach the connector with the receiver, the base including a wall surface that defines a transverse passageway extending from a distal facing opening to a lateral opening, the transverse passageway being isolated from the implant cavity, and a securing element disposable in the passageway and engageable with the stop; and a spinal rod engageable with the spinal implant.

* * * * *